(12) United States Patent
Mitchell et al.

(10) Patent No.: US 7,046,011 B2
(45) Date of Patent: May 16, 2006

(54) HIGH EFFICIENCY ELECTROSTATIC AIR SAMPLER

(75) Inventors: Bailey W. Mitchell, Watkinsville, GA (US); Richard K. Gast, Watkinsville, GA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 70 days.

(21) Appl. No.: 10/670,575

(22) Filed: Sep. 26, 2003

(65) Prior Publication Data

US 2005/0068040 A1   Mar. 31, 2005

(51) Int. Cl.
*G01R 29/12* (2006.01)
*C12Q 1/24* (2006.01)

(52) U.S. Cl. ......................................... 324/457; 435/30
(58) Field of Classification Search ................ 324/457; 435/30; 95/57
See application file for complete search history.

(56) References Cited

U.S. PATENT DOCUMENTS

| | | | |
|---|---|---|---|
| 5,855,652 A | 1/1999 | Talley | |
| 6,101,886 A | 8/2000 | Brenizer et al. | |
| 6,126,722 A | 10/2000 | Mitchell et al. | |
| 6,156,212 A | 12/2000 | Rader et al. | |
| 6,217,636 B1 | 4/2001 | McFarland | |
| 6,386,015 B1 | 5/2002 | Rader et al. | |
| 6,478,856 B1 | 11/2002 | Leibholz et al. | |
| 6,514,721 B1 | 2/2003 | Spurrell | |

OTHER PUBLICATIONS

Research International, "SASS 2000 Plus Smart Air Sampler System", SASS 2000 Plus specs (002211) , p. 65.
Larson, C., et al., "Evaluation of the Burkard Cyclonic Spore Sampler for Collection Efficiency of Ascospores", *Plant Disease*, vol. 85, pp. 1249-1252.
Mehta, S., et al., "Evaluation of Portable Air Samplers for Monitoring Airborne Culturable Bacteria", *AIHAJ*, vol. 61, pp. 850-854, 2000.
Fung, D., et al., "HACCP and Air Sampling", *Bioscience World*, vol. 4, (1) , pp. 1-4, Summer 2000.
American Biological Safety Association, "Biological Contamination of the Building Environment", *Journal of the American Biological Safety Association*, vol. 5, (1) , pp. 22-23, 2000.
Decker, H., et al., "Advances in Large-Volume Air Sampling", *Contamination Control Magazine*, Aug. 1969 issue.
Gerone, P., et al., "Assessment of Experimental and Natural Viral Aerosols", *Bacteriological Reviews*, vol. 30, pp. 576-588, Sep. 1966.
Parvaneh, S., et al., "A New Method for Collecting Airborne Allergens", *Allergy*, vol. 55, pp. 1148-1154, 2000.

(Continued)

*Primary Examiner*—Anjan Deb
*Assistant Examiner*—Timothy J. Dole
(74) *Attorney, Agent, or Firm*—John D. Fado; Gail E. Poulos

(57) ABSTRACT

An electrostatic sampling device with no moving parts is useful for high efficiency sampling of airborne particulates, especially microorganisms. It is easy to use and disinfection can be simplified by partial or total water-tight enclosure of all electronic parts.

10 Claims, 11 Drawing Sheets

Settling  Electrostatic  Impaction (100 L)

HIGH EFFICIENCY ELECTROSTATIC AIR SAMPLER

BACKGROUND OF THE INVENTION

1. Field of the Invention

This invention relates to an electrostatic air sampling devices for high efficiency sampling of bioaerosols that can include airborne bacteria, viruses, fungi, spores, etc. and methods for using the devices.

2. Description of the Related Art

Numerous devices are available for collection of airborne microorganisms (bioaerosols) from outdoor and indoor environments. Some examples include impingers, impactors, centrifugal devices, cyclone devices, and forced-air electrostatic devices. Bioaerosols include microorganisms such as bacteria, viruses, fungi, fragments of microorganisms, air-borne pollens, toxins, etc. Bioaerosols can result from natural processes such as pollen releases by plants, or from human activities by inadvertent releases such as in food processing plants, poultry hatcheries, operating rooms, communicable diseases, etc., or intentional releases such as agricultural or battlefield releases. The concentration of specific bioaerosols of interest can be quite low and the challenge usually is to collect viable microorganisms in a large air sample.

One group of samplers are impingers which collect samples in liquid. The longer an impinger is operated the greater the loss of viable cells due to aeration. Collection directly into liquid provides some protection for microorganisms versus other methods and allows initiation of damage repair caused by the rigors of aerosolization, aerosol residence time, and collection. Aggregates of cells which would grow as a single colony collected by an impactor sampler, are broken up in the impinger liquid. This makes it possible, through appropriate titrations, to enumerate the total culturable cell per volume of air. The AGI-30 impinger is an all-glass unit which draws aerosols through an inlet tube curved to simulate the human nasal passage. A one-half atmosphere vacuum is drawn across the tube so that a choked-sonic flow condition is maintained with a typical flow rate of about 12.5 L/min. This flow rate has been found to be useful for collecting microbial particles in the respirable range of about 0.8 to 15 μM. The sample is directed into a collecting medium of water. The very low intake air flow rate can be a drawback especially if very low concentrations of particulates in the environment need to be sampled during a short time such as the typical 30-minute maximum operational time of the AGI-30. Some impingers have been developed to improve the viability of collected bioaerosols.

Another type of sampler is an impactor sampler which is useful for determining the size distribution of airborne particles. The sampler impacts particles onto agar surfaces using centrifugal forces. Collection by impaction makes it possible to enumerate the number of colony forming units (CFU) per unit volume of air. These evaluation methods rely on multiplication of microbial cells on nutrient media and therefore cannot detect microorganisms unable to grow because the media is inappropriate or the cells have been damaged by the stresses of aerosolization and/or collection. One example is the Andersen multi-stage cascade impactor which has a similar collection efficiency for microorganisms to that of the AGI-30 impinger. It provides relatively low intake air-flow rates of about 28.3 L/min. The Andersen six-stage and two-stage viable particle sizing impactors use vacuum pumps for operation which are noisy, heavy, and require an a.c. electrical source which limits usage in locations where electricity is not available or where size and weight must be minimized. Other examples of impactor samplers can be found in U.S. Pat. No. 6,514,721 (Spurrel, Feb. 4, 2003), U.S. Pat. No. 6,217,636 (McFarland, Apr. 17, 2001), and U.S. Pat. No. 6,101,886 (Brenizer et al., Aug. 15, 2000).

Some centrifugal samplers are lightweight and self-contained. In one model, airborne particles are impacted on an agar strip. Such samples can be useful for collecting samples in locations that are difficult to monitor with other methods such as inside duct work. Collection efficiency is a function of particle size and tends to be greater for larger sized particles.

Slit to agar samplers aspirate air by a vacuum through a slit and the airborne particles are impacted onto a rotating agar surface which allow differences in the aerial bioburden over time to be observed. This type of sampler may give lower counts versus impactors or impingers and may not be efficient for trapping small particles or useful in areas that have low numbers of culturable particles.

Cyclone samplers separate particles from a main flow and concentrate them in an adjacent recirculating chamber without impact. The main particle-laden flow follows a wall that curves away from the original flow direction. Although the wall forms the inner boundary of the main flow, its outer boundary is formed by an adjacent flow, often a confined recirculating flow, into which particles are transferred by centrifugal action. The particles are separated from the main flow by crossing a dividing streamline that separates the main flow stream from an adjacent flow stream. If a confined recirculating chamber geometry is used, particle concentrations in the recirculating region can be greatly increased relative to the main stream. Some of the drawbacks are turbulent mixing produced by shear-layer roll-up which can limit particle-concentration enhancement at high flow Reynolds numbers, and difficulty in sample removal from the recirculating chamber for analysis. Examples of this technology can be found in U.S. Pat. No. 6,156,212 and the Research Institute International flyer on the SASS 2000 Smart Air Sampler.

Filtration samplers are also used to collect culturable cells onto solid filters or soluble materials. Membrane filters have been found to recover similar numbers of fragile microorganisms to those recovered by agar surface impaction devices. Solid filter samplers may adversely influence the survival of airborne microorganisms due to impaction and dessication, and they recover fragile microorganisms with an efficiency similar to that of agar surface impaction devices. The use of gelatin air filters increases survival by decreasing the effect of dessication. Pore size must be carefully selected so those particles carrying bacteria, viruses, and fungi are retained on the filter.

Collection of culturable airborne particles through precipitation is achieved by samplers that collect air and electrostatically or thermally precipitate particles onto a thin flowing film of collecting fluid. Most are used for qualitative determination of pollen and fungal spores for use in allergenic evaluations. Examples of these type of collectors are the Rotorod, Burkard, LVS, and Samplair samplers. See also U.S. Pat. No. 5,855,652 and Allergy 2000, Volume 55, 1148–1154, 2000.

While various systems have been developed for sampling of airborne bacteria, viruses, fungi, spores, etc., there remains a need in the art for a more effective system for sampling viable and non-viable microorganisms and particles from bioaerosols using a device that causes minimal damage to viable organisms, has no moving parts, has a high collection efficiency, and is easily transported and disinfected. The present invention described below meets these needs and is different from the related art systems.

SUMMARY OF THE INVENTION

It is therefore an object of the present invention to provide a high efficiency electrostatic sampling device 10 for sampling airborne particulates, especially microorganisms, which includes at least one discharge electrode 6, a DC powered high voltage power supply 4, and a collector means 8.

Another object of the present invention is to provide a high efficiency electrostatic sampling device 10 for sampling airborne particulates which has at least one discharge electrode 6, a DC powered high voltage power supply 4, a collector means 8, and media 18 for the desired sampled microorganisms.

A still further object of the present invention is to provide a high efficiency electrostatic sampling device 10 for sampling airborne particulates, especially microorganisms, which includes at least one discharge electrode 6, a DC powered high voltage power supply 4, a voltage regulator 3, at least one battery 1, collector means 8, means for grounding 9 and media 18.

Another object of the present invention is to provide a high efficiency electrostatic sampling device 10 for sampling airborne particulates, especially microorganisms, which includes at least one discharge electrode 6, a DC powered high voltage power supply 4, a voltage regulator 3, at least one battery 1, collector means 8, means for grounding 9, media 18, and a first sealed compartment 11.

A still further object of the present invention is to provide a high efficiency electrostatic sampling device 10 for sampling airborne particulates, especially microorganisms, which includes at least one discharge electrode 6, a DC powered high voltage power supply 4, a voltage regulator 3, at least one battery 1, collector means 8, means for grounding 9, media 18, a first sealed compartment 11, and a second sealed compartment 12.

Another object of the present invention is to provide a high efficiency electrostatic sampling device 10 for sampling airborne particulates, especially microorganisms, which includes at least one discharge electrode 6, a DC powered high voltage power supply 4, at least one battery 1, collector means 8, means for grounding 9, media 18, and a first sealed compartment 11.

A still further object of the present invention is to provide a high efficiency electrostatic sampling device 10 for sampling airborne particulates, especially microorganisms, which includes at least one discharge electrode 6, a DC powered high voltage power supply 4, at least one battery 1, collector means 8, means for grounding 9, media 18, a first sealed compartment 11, and a second sealed compartment 12.

Another object of the present invention is to provide a high efficiency electrostatic sampling device 10 for sampling airborne particulates, especially microorganisms, which includes at least one discharge electrode 6, a DC powered high voltage power supply 4, a voltage regulator 3, a 120 volt ac powered adaptor with a DC output, collector means 8, means for grounding 9 and media 18.

Another object of the present invention is to provide a high efficiency electrostatic sampling device 10 for sampling airborne particulates, especially microorganisms, which includes at least one discharge electrode 6, a DC powered high voltage power supply 4, a 120 volt ac powered adaptor with a DC output, collector means 8, means for grounding 9 and media 18.

A still further object of the present invention is to provide a high efficiency electrostatic sampling device 10 for sampling airborne particulates, especially microorganisms, which includes at least one discharge electrode 6, a DC powered high voltage power supply 4, a voltage regulator 3, a 120 volt ac powered adaptor with a DC output, collector means 8, means for grounding 9 and media 18.

Further objects and advantages of the invention will become apparent from the following description.

DETAILED DESCRIPTION OF THE INVENTION

Collection of bioaersols is important for general sanitation, health research, and disease outbreaks-especially for detecting pathogens. Bioaerosol sampling in animal housing, processing areas, hatcheries, etc. can identify the presence of *Salmonella, E. coli*, Influenza, Newcastle disease virus, etc. In hospitals, hotels, schools and other public areas, sampling can identify *E. coli, Salmonella*, tuberculosis, etc. Bioaerosol sampling can also be used to detect the presence of spores of *Aspergillus*, anthrax, molds, etc.

Most efficient samplers to date are seldom used due to complexity, size, cost, and/or difficulty in disinfecting. The most commonly used samplers are settling plates which can detect moderate levels of bacteria or mold but may require several hours of exposure resulting in dehydration of media and lowered viability of organisms. Settling plates are also prone to miss many of the smaller particles which tend to stay in suspension. Desired sampler characteristics include a device that is easy to use, that is capable of detecting very low levels of microorganisms, such as for example, about one microorganism per cubic meter; is easy to disinfect, and can directly collect microorganisms onto solid or liquid media or solid surfaces with limited damage to the microorganisms. The sampling device should be lightweight, small, and easy to transport.

The present invention is an electrostatic device for high efficiency sampling of airborne bacteria, viruses, and spores which uses any type grounded, conductive material such as, for example, solid or liquid culture media, water, or conductive solids like metal disks. The device can be battery powered and it can also use a metal collector with no media, and has no moving parts. In some embodiments for the present invention, disinfection is simplified by a water-tight enclosure of all electronic parts except the sampling plate. Even when the batteries are exposed, as shown in FIG. 1, disinfection is easy.

Figure 5:
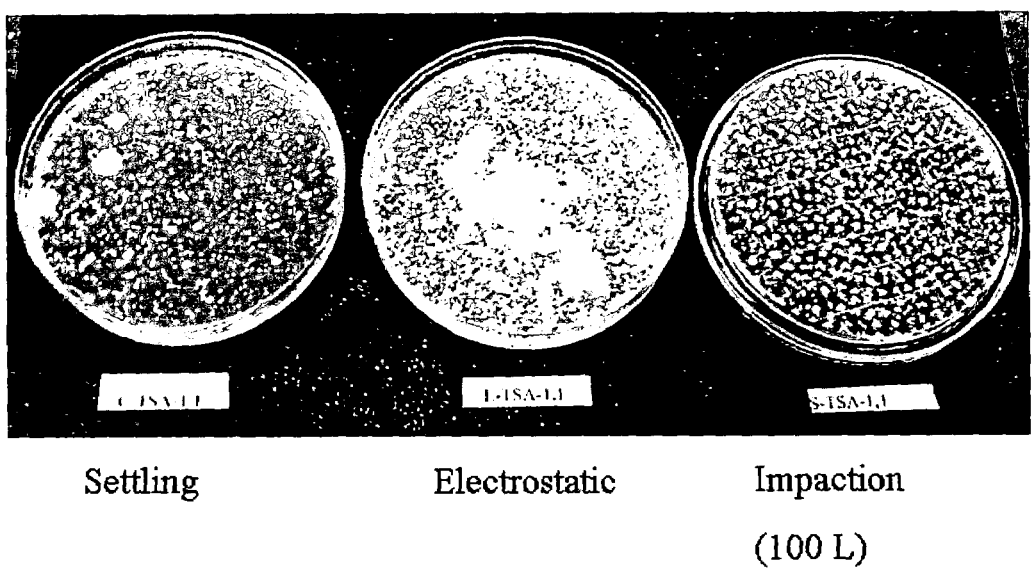
FIG. 5 is a photograph comparing total bacteria collected using device 10 (electrostatic), a settling plate (settling), and a SAS-90 Impaction sampler (impaction-100 L) using TSA agar. The devices were placed beneath an outlet duct of a poultry house exhaust system for about 1.1 minutes.

Device 10 (FIGS. 1–3) creates a strong negative electrostatic field close to a collector means 8, such as for example a media plate containing a culture medium, causing airborne particles within a few inches of the device to be negatively charged and pulled to the grounded media. This action causes air to be moved rapidly toward the plate as it is drawn along with the particulates giving the effect of a medium volume air sampler without the need for a mechanical fan. The present invention has an equivalent air flow of at least about 100 liters/minute (See comparison to 100 L, 1.1 minutes forced air sampler in FIG. 5) which theoretically if extended to about two hours can provide the equivalent of a High Volume Air Sampler, e.g. could sample about half of the air in a typical 3 meter wide×3 meter long×2.7 meter high office in a two hour period. Besides drawing nearby particulates to the media, device 10 also captures microorganisms and spores and binds them strongly to the grounded, conductive material such as, for example, solid or liquid media which can be optimized for the desired type or class of organism. The media provides nutrients to maintain the microorganisms in a viable condition until the sampling and subsequent incubation or processing period is completed. The essential requirement for media 18 is that it be at least as conductive as water. Acceptable grounded conductive material such as, for example, media or collection surfaces include water, cell culture media, microbiological media, any metal material, conductive carbons, etc.

If non-viable organisms are acceptable or if the organisms are able to stay viable for a few hours without nutrients, air samples can be collected on, for example, a dry metal plate. The collected particulates would then be washed into another container or swabbed for identification by a method such as by PCR for example. The diameter or size of the collector means 8, in this case, should be that which maintains a useful collection efficiency, determination of which is within the ordinary skill in the art given the detailed description of the present invention.

Figure 1:
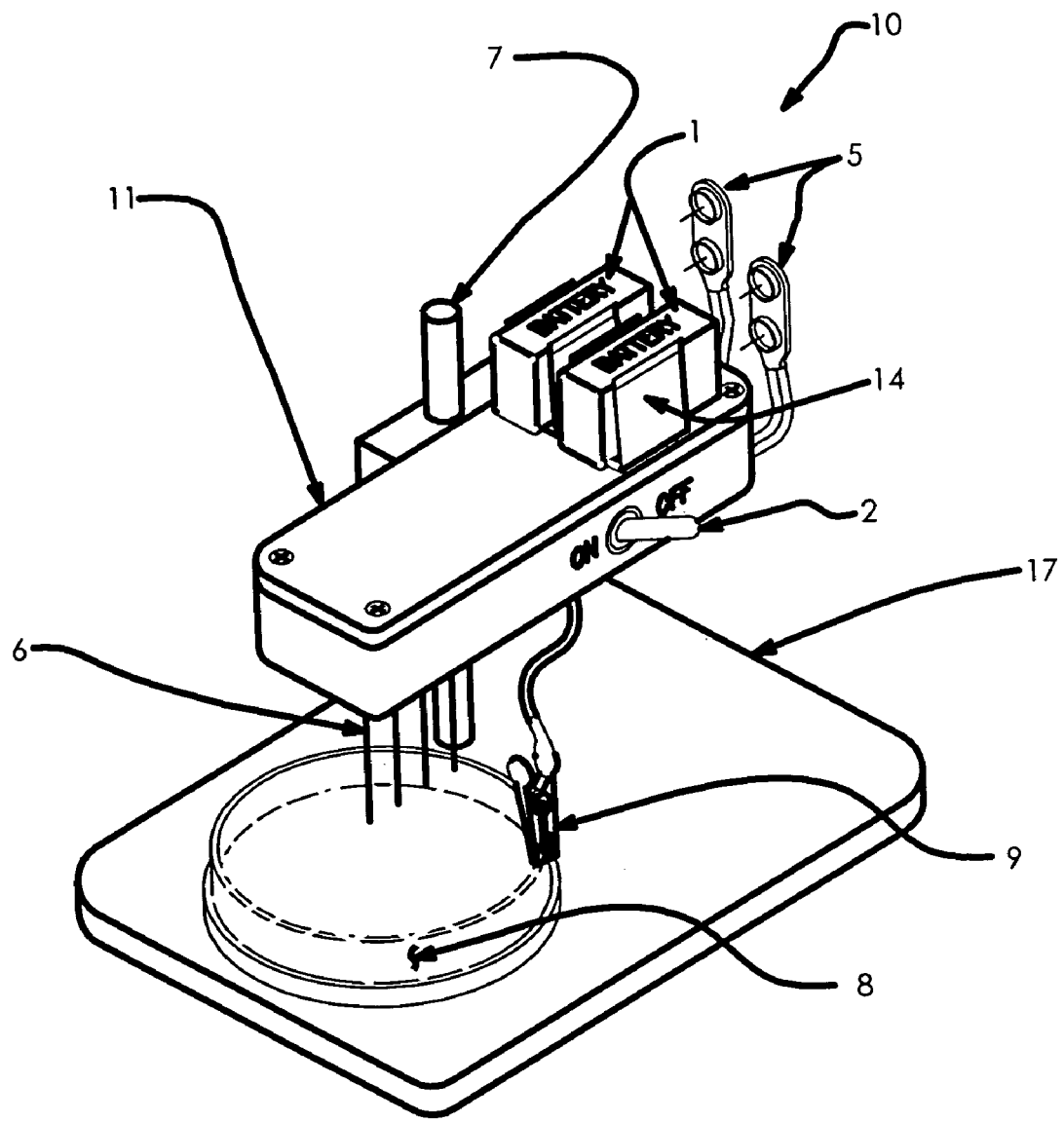
FIG. 1 is a drawing of one embodiment of the present invention showing device 10 including batteries 1, means for attaching batteries 5, external holding means 14, power switch 2, discharge electrodes 6, means for adjusting electrode height 7, collector means 8, means for grounding 9, first sealed compartment 11 and base 17.
Figure 2:
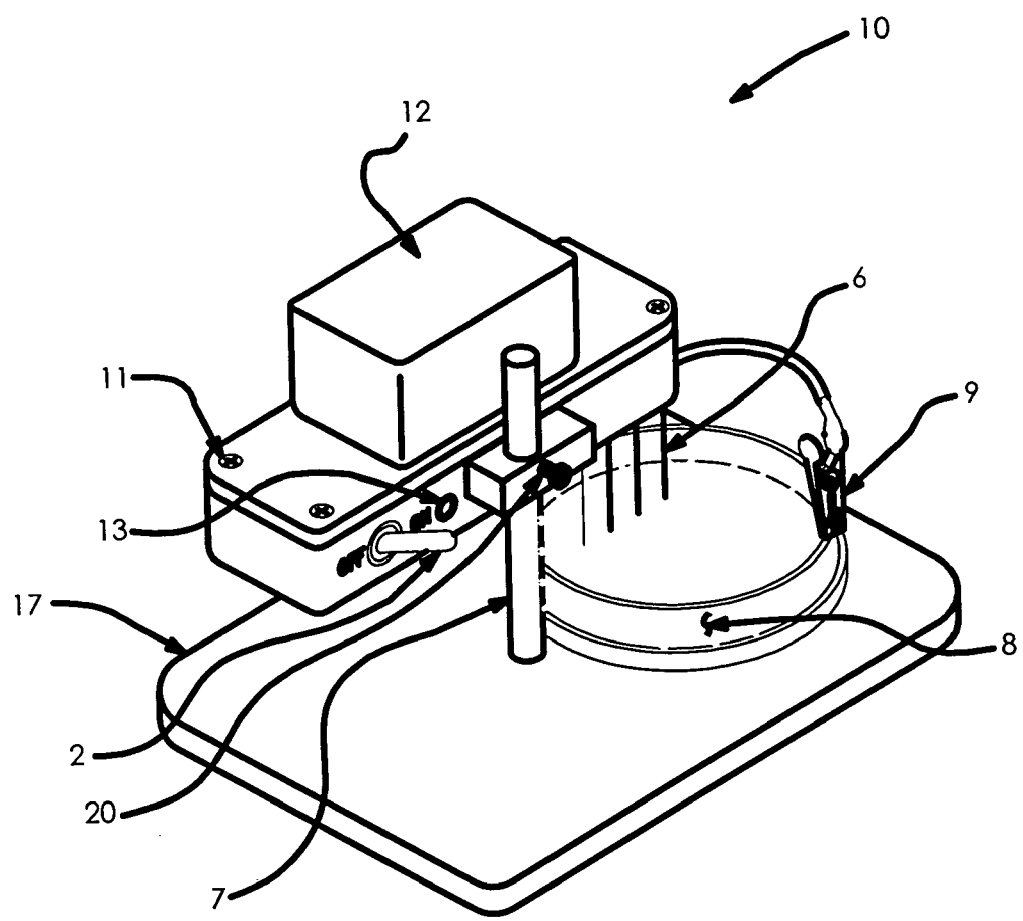
FIG. 2 is a drawing showing one embodiment of the present invention showing device 10 including power switch 2, power light indicator 13, discharge electrodes 6, means for adjusting electrode height 7, set screw 20, collector means 8, means for grounding 9, first sealed compartment 11, second sealed compartment 12 and base 17.
Figure 3:
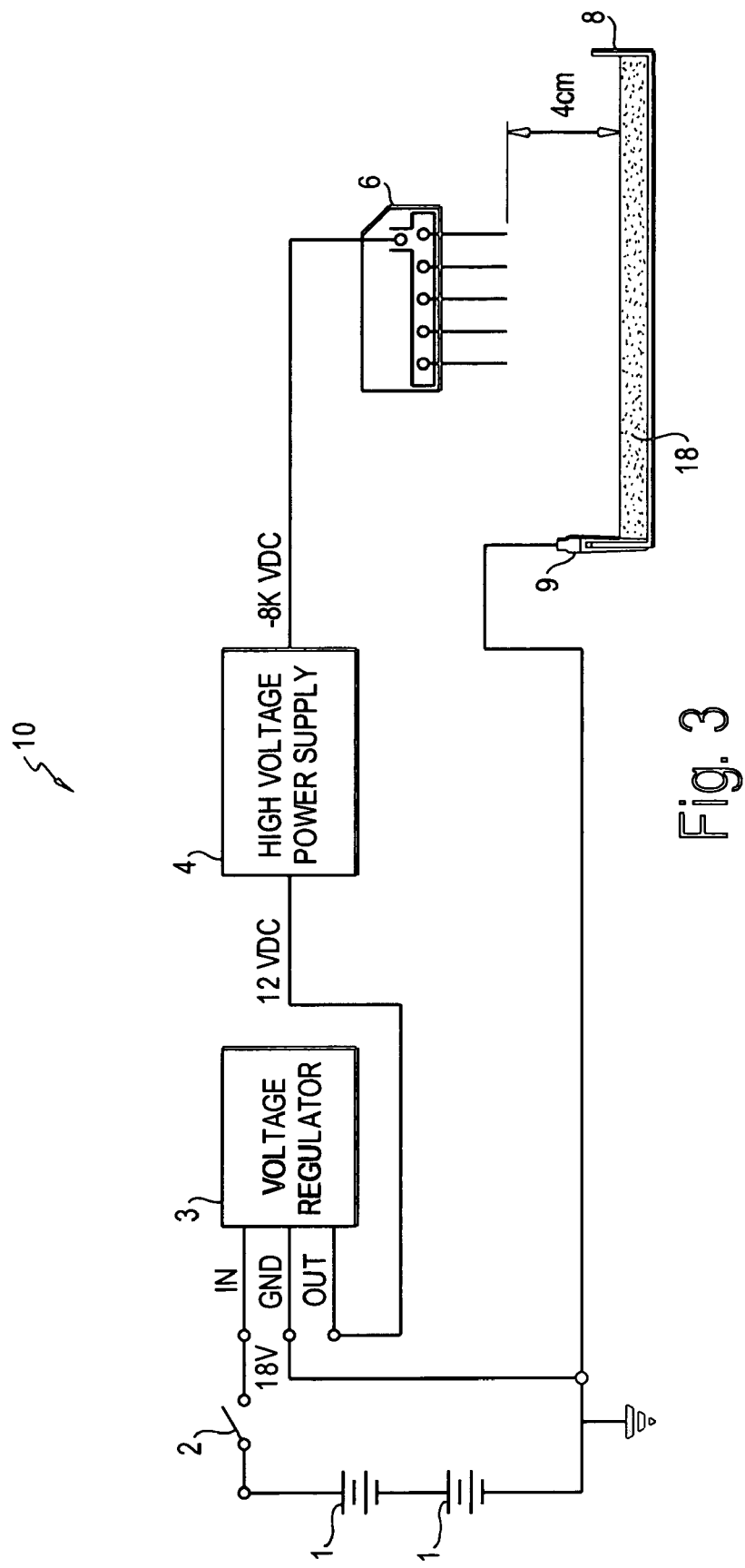
FIG. 3 is a drawing showing a circuit diagram of device 10 including batteries 1, power switch 2, voltage regulator 3, DC powered high voltage power supply 4, discharge electrodes 6, collector means 8, means for grounding 9, and media 18.

Means for grounding 9 provides a connection for the grounded, conductive material to the ground side of HV power supply 4 resulting in a grounded collector means 8 in the vicinity of negatively charged particulates which will be drawn to grounded media 18 (FIGS. 1–3). A variety of means for grounding 9 can be used, such as, for example clips, pins, small disks, etc. In FIGS. 1–3, a clip is shown, which allows for easy and secure connection to the side of collector means 8, which in the figures is an agar plate, such that the end of the clip is pushed all the way to the bottom of the media or water. If a grounded, conductive material, such as a metal plate or cup collector is used, means 9 is connected to the edge of the plate or cup.

In one embodiment of the present invention, Electrostatic Sampling device (ESD) 10, while exemplified for poultry houses, can be used in any area where bioaerosol sampling is desired. Electrostatic Sampling device 10 (FIG. 1) includes discharge electrodes 6, at least one battery 1, means for attaching batteries 5, external battery holding means 14, discharge electrodes 6, voltage regulator 3, DC powered high-voltage power supply 4, power switch 2, optionally a means for adjusting electrode height 7 above a media source, collector means 8, means for grounding 9, first sealed compartment 11, and base 17.

In another embodiment of device 10 (FIG. 2), high-voltage power supply 4, power switch 2, and regulator 3 are stored in a first sealed compartment 11. The at least one battery 1 is stored in a second sealed compartment 12. Sealed compartment 11 and second sealed compartment 12 can be made of any non-conductive material that can be easily disinfected. Additionally, this embodiment can optionally include a power light indicator 13 and a set screw 20.

In a third embodiment, both the batteries and electronics are exposed (not shown). Furthermore, regulator 3 can be optional in any embodiment of the present invention.

Regulated dc high voltage (HV) power supply 4, driven by at least one standard 9 volt battery 1, provides a constant high voltage output of about between −7 to −8 kVdc (FIG. 3). A 12V high voltage power supply 4 can be operated by about 12V to about a 30V input to provide a regulated 12V output if used with a voltage regulator 3. HV power supply 4 can also operate with voltage inputs as low as about 7 Vdc. Output of the HV supply 4 will drop from about −8 kVdc with about a 12V input down to about −7kVdc with about a 9 Vdc input. If using about a 9 volt input, for example, there is an initial output of about −7.7 Vdc which steadily drops to about −5.3 kVdc over about 5 hours which is still a substantial charge and sufficient to attract particulates, including microorganisms, to the grounded, conductive material such as media 18. Voltage regulator 3 (FIG. 3) is operatively connected and placed between the at least one battery 1 and HV power supply 4 through insulated wires. The use of regulator 3 in device 10 results in some loss of power through inefficiency of regulator 3 itself and heat loss. If using, for example, an 18V input consisting of two 9V batteries 1, in series, regulator 3 will maintain a 12V input to HV supply 4 for approximately 5 hours with about a −8 kV peak output. The high voltage output from supply 4 is applied to sharp-pointed discharge electrodes 6 which generate a strong electrostatic field between discharge electrodes 6 and the grounded, conductive material such as media 18 which is contained in a standard agar plate located approximately 4 cm below electrodes 6 in a permanently mounted collector means 8.

In an embodiment of the present invention, device 10 can be operated directly without a regulator using a battery or a series of batteries 1 which provide about 9V to about 12V. For example, one 9V battery 1 will operate device 10 for about 5 hours, five 9V batteries 1 in series will operate device 10 for about 25 hours. This eliminates the power loss when using a regulator resulting in a longer battery life and longer operation of device 10. The at least one battery 1 is operatively connected to voltage regulator 3 in one embodiment of the present invention or directly to HV power supply 4. A power switch 2, when used, is operatively connected to the at least one battery 1 and regulator 3 or HV power supply 4. The at least one battery 1 can be located within a second sealed compartment 12 on top of a first sealed compartment 11 (FIG. 2), secured with external holding means 14 (FIG. 1), such as for example, battery clips, onto top fo first sealed compartment 11, etc. The attachment of the at least one battery 1 to device 10 is within the ordinary skill in the art. Battery connection through means for attaching batteries 5, to HV power supply 4 can be made by clips, screw terminals, pressure connections, etc (FIG. 1). Any technique for connecting the batteries can used which allows for a firm and stable connection and can be easily disinfected.

In another embodiment, device 10 can be operated with a 120V ac powered adaptor with an appropriate DC voltage output for extended operational times when ac power is convenient. Device 10 can also be configured for operation by either ac adaptor or by battery, such that, for example, if ac power is removed the device will automatically switch to battery power.

Electrostatic air sampling device 10 includes at least one discharge electrode 6. Electrodes 6 may be connected together on a printed circuit board or can be connected by other means such as soldering onto a rod or plates, etc., which is well within the ordinary skill in the art. Device 10 can be adjustably mounted onto means for adjusting 7 such that the electrode points are about 1 cm to about 8 cm, preferably about 4 cm, above the grounded conductive material. Furthermore, device 10 can be permanently mounted at a desired distance above grounded conductive material.

Electrostatic air sampling device is operated with at least about −5,000 volts dc on electrodes 6 with about −8,000 volts dc preferred. However, any voltage producing a space charge which causes the collection of bioaerosol particles onto a medium can be used. It is preferred to use voltages below about −8,000 volts d.c. since substantially higher voltages may cause excessive cell damage to the collected organisms. The number of electrodes 6 is dependent on the desired space charge magnitude and the size of the collection area, determination of which is well within the ordinary skill in the art based on the present detailed description. If more than one electrode is used, they are spaced about 1 cm apart. Five electrodes, for example, evenly spaced about 1 cm apart has been shown to provide excellent collection efficiency and even microorganism distribution when used with standard-sized agar plates in poultry houses and office type environments.

Device 10 can also include base 17 which allows device 10 to be placed on a surface. Device 10 can also be mounted on a wall or suspended from a ceiling using any means within the ordinary skill in the art.

In operation, device 10 is placed in an area to be tested, such as, for example, near the outlet of a poultry house exhaust system duct, in a poultry caged layer room, in animal housing, in a food processing area, in hospitals, hotels, schools, public areas, etc. Device 10 is powered either by at least one battery 1 or by an AC adaptor with a DC output if an electrical outlet is available and long term use without batteries is desired. At least about 9 volts of power is supplied to a high voltage power supply 4. The power can be optionally directed through a voltage regulator 3 and then to power supply 4. High voltage power supply 4 provides a negative high voltage output of about −7 to about −8 kVdc to at least one discharge electrode 6 to produce a strong electrostatic field between at least one electrode 6 and a grounded conductive material in most embodiments. This causes airborne particles within a few inches of device 10 to be pulled to the grounded, conductive material such as media 18 or other grounded conductive non-media such as for example water or a metal collector. This action causes air to be moved rapidly towards the grounded conductive material as it is drawn along with the particulates, such as microorganisms and spores, giving the effect of a medium volume air sampler without the need for a mechanical fan. In most cases, if it is desired to collect viable microorganisms or spores, collector means 8 will contain a media 18. The media will provide nutrients to maintain the microorganisms or spores in a viable condition until sampling and subsequent incubation or processing is completed. If the organisms are able to stay viable for a few hours without nutrients, or if non-viable organisms are not a concern, air samples can be collected on, for example, a dry metal plate.

The following examples illustrate the use of the invention. They are intended to further illustrate the invention and are not intended to limit the scope of the invention as defined by the claims.

EXAMPLE 1

Figure 4:
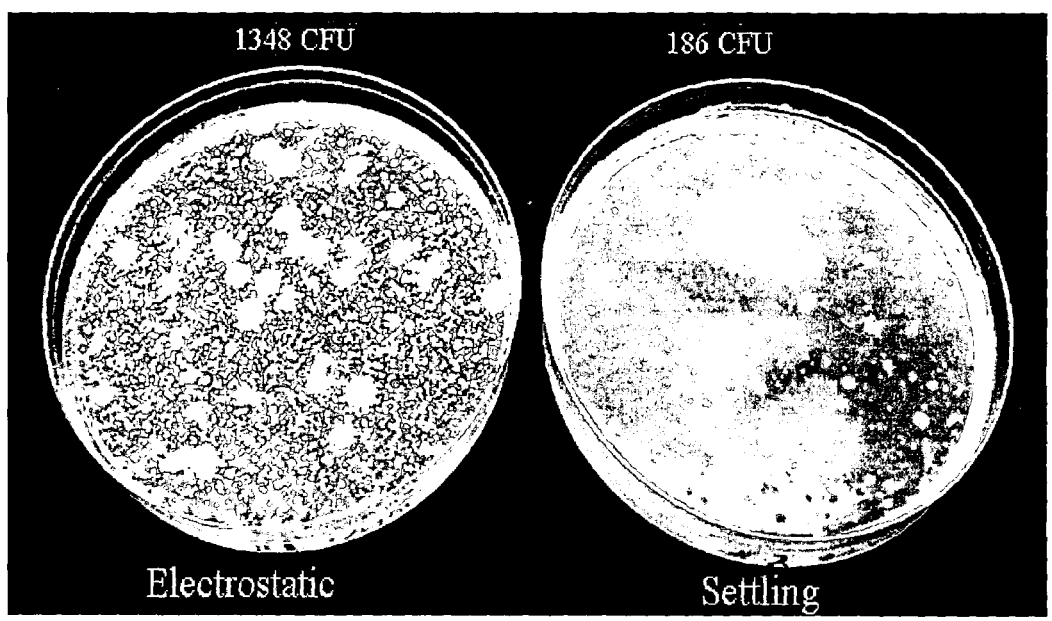
FIG. 4 is a photograph comparing total bacteria collected using device 10 (electrostatic)(1348 CFU) and a settling plate (settling) (186 CFU) using TSA agar. The devices were placed beneath an outlet duct of a poultry house exhaust system for about one minute.
Figure 6:
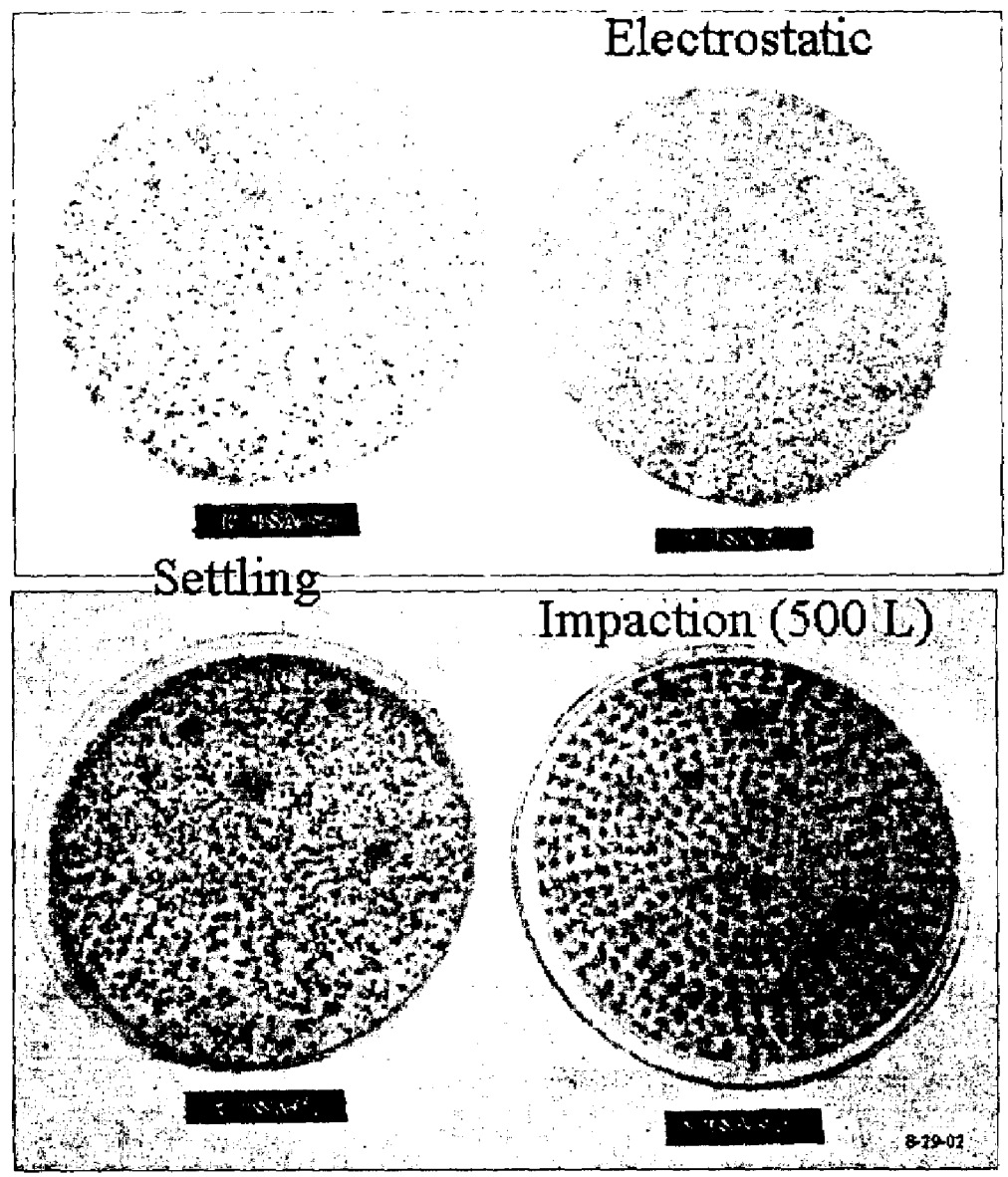
FIG. 6 is a photograph comparing total bacteria collected using device 10, settling plates, and a SAS-90 Impaction sampler (impaction-100 L) using TSA agar. The devices were placed beneath an outlet duct of a poultry house exhaust system for about 5.6 minutes.
Figure 7:
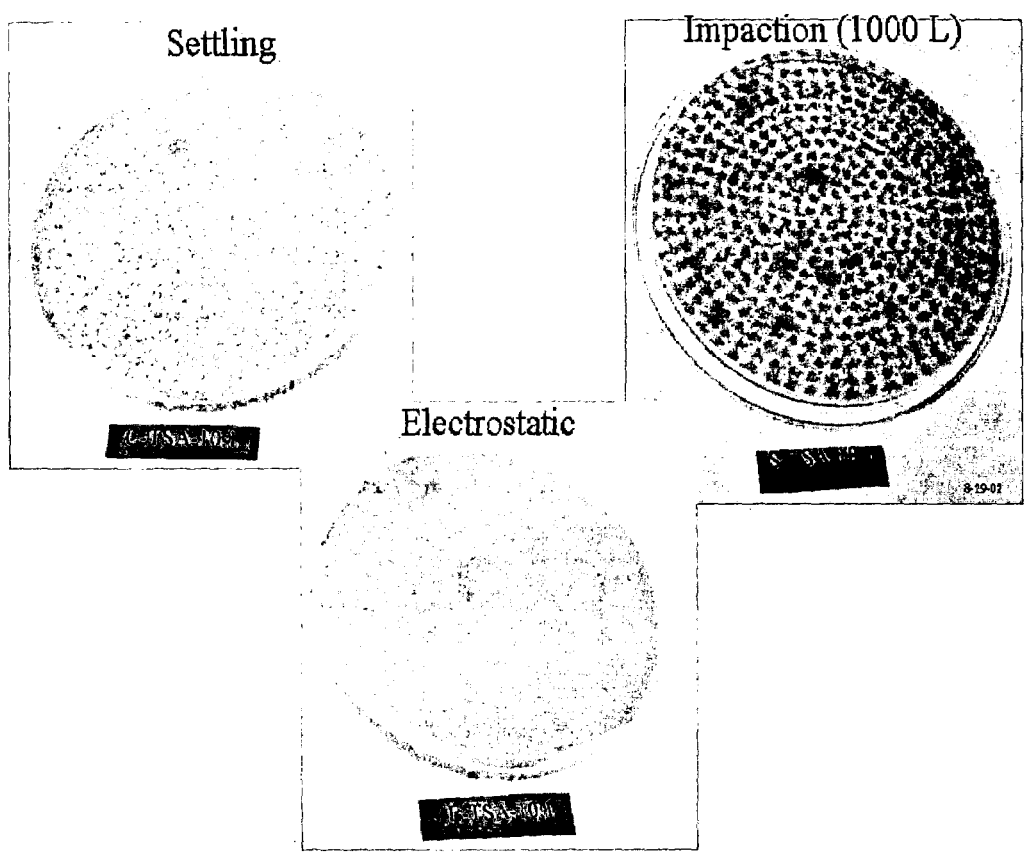
FIG. 7 is a photograph comparing total bacteria collected using device 10 (electrostatic), a settling plate (settling), and a SAS-90 Impaction sampler (impaction-100 L) using TSA agar. The devices were placed beneath an outlet duct of a poultry house exhaust system for about 11.1 minutes.
Figure 8:
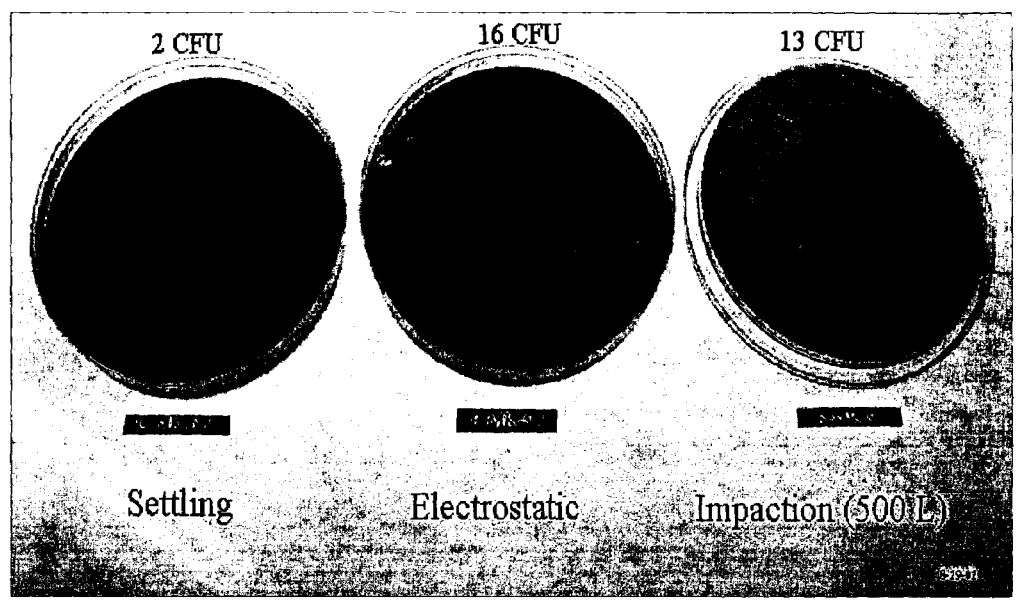
FIG. 8 is a photograph comparing Enterobacteriaceae collected using device 10 (electrostatic), a settling plate (settling), and a SAS-90 Impaction sampler (impaction-500 L) using MacConkey agar. The devices were placed beneath an outlet duct of a poultry house exhaust system for about 5.6 minutes.
Figure 9:
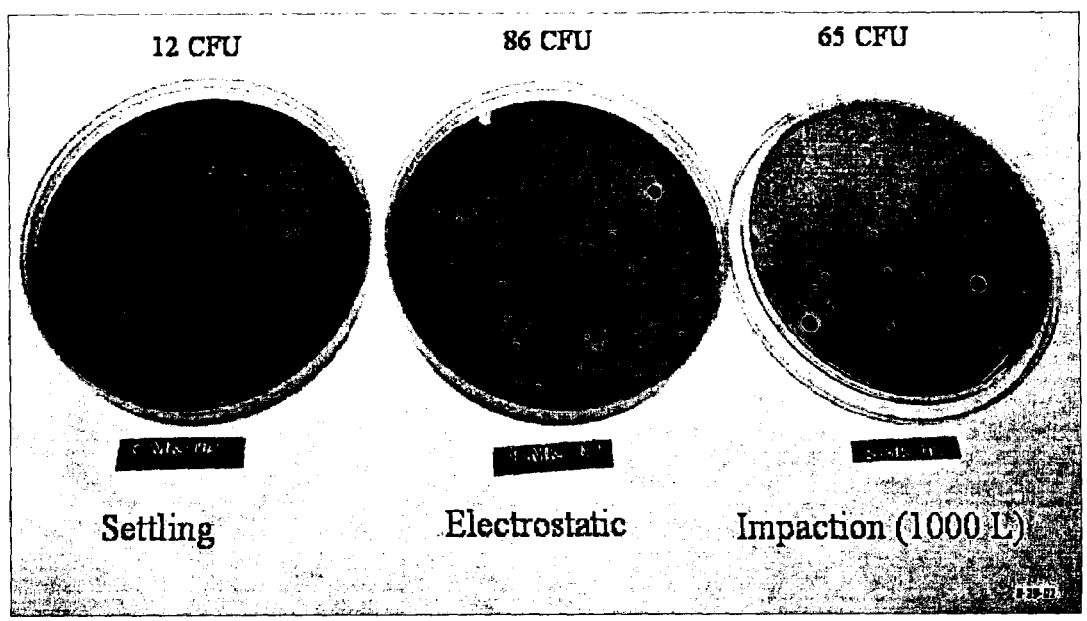
FIG. 9 is a photograph comparing Enterobacteriaceae collected using device 10 (electrostatic), a settling plate (settling), and a SAS-90 Impaction sampler (impaction-1000 L) using MacConkey agar. The devices were placed beneath an outlet duct of a poultry house exhaust system for about 11.1 minutes.

Poultry house exhaust air sampling was performed using settling plates, an SAS-90 impaction sampler, and device 10 of the present invention as depicted in FIG. 1. The devices were placed on a platform about 36 inches below the opening of the exhaust duct with the settling plates placed behind the other sampling devices. Trypticase Soy Agar (TSA)(for total bacterial counts) and MacConkey (for gram negative bacteria such as, for example, *Salmonella, E. coli*, etc.) plates for the three types of samples were exposed for about 1.1, 5.6, and 11.1 minutes corresponding to about 100 liters, 500 liters, and 1,000 liters for the SAS-90 sampler. Colony counts for the TSA plates were too numerous to count even with the about 1.1 minute sample (FIG. 4), but visual observations clearly showed the concentration of colonies for device 10 of the present invention (Electrostatic—FIG. 5) to be higher than those with the SAS-90 impaction sampler (Impaction plate—FIG. 5) and much higher than for the settling plates (Settling—FIG. 5). These relative comparisons were the same for the about 5.6 (FIG. 6) and the about 11.1 (FIG. 7) minute samples with correspondingly higher concentrations with increasing time. With the MacConkey plates at about 5.6 minutes (FIG. 8), device 10 of the present invention had counts significantly higher than the SAS-90 (about 16 CFU vs. about 13 CFU and about 8× higher than the settling plates (about 16 CFU vs about 2 CFU). At about 11.1 minutes (FIG. 9), device 10 of the present invention had counts which were about 86 CFU vs. 65 CFU for the SAS-90 and about 12 CFU for the settling plates.

EXAMPLE 2

The effectiveness of device 10 for detecting the presence of airborne *S. enteritidis* was tested in a room containing experimentally infected laying hens. In two replicate trials, 36 39-week old laying hens from the USDA-Agricultural Research Service Southeast Poultry Research Laboratory's specific-pathogen-free flock of single-comb white leghorn chickens were housed individually in laying cages in a disease-containment facility. The hens were distributed evenly throughout two tiers of cages in a single room and provided with water and pelleted feed ad libitum. The floor of this room was cleaned at weekly intervals to remove accumulated waste and debris including manure, feathers, and dust. All hens were inoculated orally with a phage type 13a isolate of *Salmonella enteritidis* (Gast et al., Avian Diseases, Volume 34, 438–446, 1990; Gast et al., Avian Diseases, Volume 34, 991–993, 1990; both herein incorporated by reference), prepared by overnight incubation at about 37° C. in tryptone soy broth (Oxoid Limited, Basingstoke, Hampshire, UK) and dilution in about 0.85% saline to yield approximately $1.2 \times 10^9$ CFU of *S. enteritidis* per approximately a 1-ml dose.

Samples of voided feces were collected from each hen and cultured for the presence of *S. enteritidis* by previously described methods (Gast et al., Avian Diseases, Volume 37, 1085–1091, 1993; herein incorporated by reference) immediately before inoculation and at about 1,2,3, and 4 weeks postinoculation.

Yolks from eggs collected immediately before inoculation and at weekly intervals after inoculation were tested for the presence of antibodies specific to *S. enteritidis* flagella by an enzyme-linked immunosorbent assay (ELISA) developed by Holt and Porter (Poultry Science, Volume 72, 2069–1078, 1993) and described previously (Gast et al., Poultry Sciences, Volume 81, 1128–1131, 2002). Post inoculation egg yolk samples were considered to be antibody-positive in this test if their ELISA absorbance values exceeded the mean absorbance value for the preincubation negative control samples by more than two standard deviations.

To test for the presence of airborne bacteria in the room containing laying hens, plates of agar media were exposed to air samples collected by three methods. All air samples were collected by placing necessary apparatus and media on top of the upper tier of cages. The first air sampling method simply involved passive exposure of uncovered plates of agar media for periods of about 20 minutes, about 1 hour, or about 3 hours. Four plates were exposed each time this test was performed. The second air sampling method employed an SAS Super 90 Impaction Air Sampler (Bioscience International, Rockville, Md.), which directed air onto the surface of agar media plates at a rate of about 90 L/minute. One plate was exposed each time this test was performed. Impaction samples were collected only for about 20 minute intervals because this is the maximum programmable time for the sampler to avoid excessive agar drying to maximize viability. The third air sampling method applied device 10 (FIG. 1) of the present invention. Samples were collected for about 20 minutes, about 1 hour, or about 3 hours.

Air samples were collected and tested four times each week for about 4 weeks post-inoculation. On two days each week, air samples were collected onto brilliant green (BG) agar (Becton Dickinson and Col., Franklin Lakes, N.J.) supplemented with about 0.02 mg/ml of novobiocin (Sigma Chemical Company, St. Louis, Mo.). This media is highly selective and differential for salmonellae. On the other two days, air samples were tested by exposure of plates of MacConkey (MAC) agar (Becton Dickinson). This medium supports the multiplication of a wide range of enteric bacteria, including salmonellae and coliforms. MAC agar samples were collected only at exposure intervals of about 20 minutes and about 1 hour to minimize bacterial overgrowth. Air samples were also taken on the day before inoculation of hens with *S. enteritidis* using only the BG agar plates.

For each replicate trial, significant differences ($P<0.05$) between air sampling methods in the mean number of total or *Salmonella* colonies recovered on agar media plates were determined by Kruskal-Wallis analysis of variance-followed by Dunn multiple comparison test. Data were analyzed in Instat biostatistics software (GraphPad Software, San Diego, Calif.). Because the statistical relationships between treatment groups were similar for the two trials, the results were combined for analysis.

Figure 11:
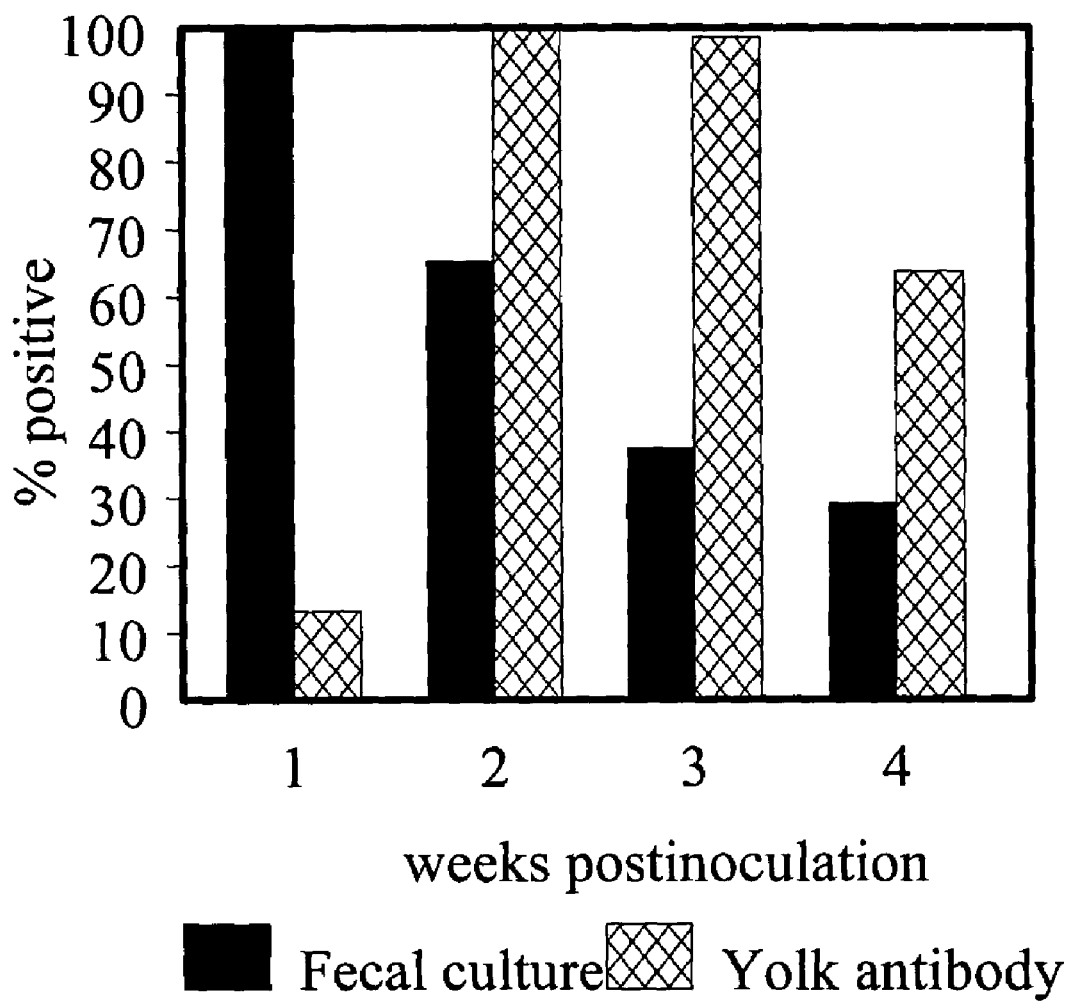
FIG. 11 shows frequency of recovery of *Salmonella enteritidis* from samples of voided feces and frequency of *S. enteritidis*-specific egg yolk antibody assay results after oral inoculation of laying hens. Samples were obtained from 36 hens in each of two replicate trials during the same period as air samples were taken.

Oral inoculation with *S. enteritidis* established both intestinal colonization measured by testing for fecal shedding and systemic infection measured by testing for specific egg yolk antibodies in the hens. No fecal samples collected before inoculation were positive for *Salmonella*, but all samples were positive for *S. enteritidis* at about 1 week after inoculation (FIG. 11). The frequency of egg yolk antibody detection decreased to about 63.8% of the hens by about 4 weeks post-inoculation.

Figure 10:
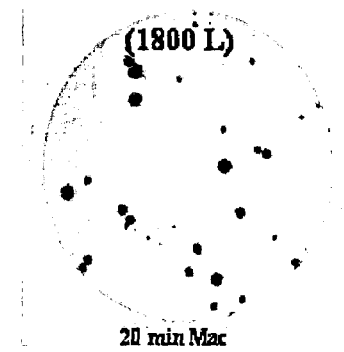
FIG. 10 is a photograph comparing *Salmonella enteritidis* and other pathogenic bacteria collected from air samples in caged layer room with birds infected with *S. enteritidis* usng device 10 and an SAS-90 Impaction Sampler using BG agar and MacConkey agar. The samples were collected for about 20 minutes and about 1 hour.
Figure 10:
Figure 10:
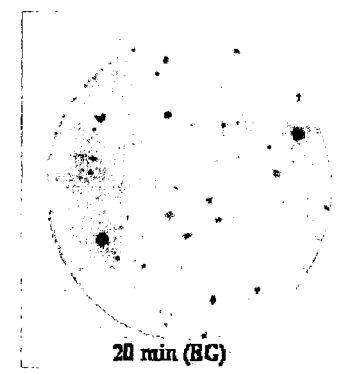
Figure 10:
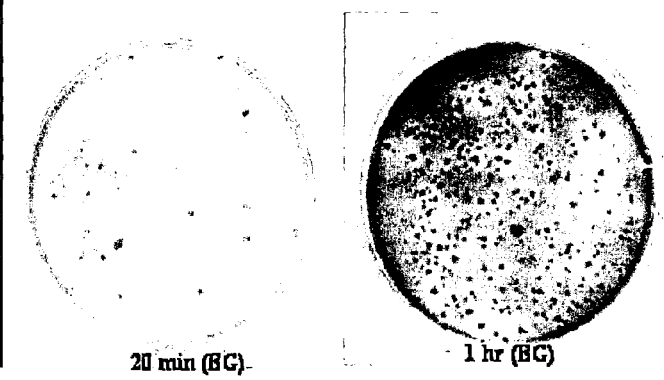

All three methods for sampling air from rooms containing infected chickens led to the collection of bacterial colonies on MAC agar plates (Table 1 and FIG. 10). The mean total bacterial counts for all combinations of air sampling methods and duration increased to peak values at about 3 weeks post-inoculation and then declined at about 4 weeks post-inoculation. Device 10 of the present invention was significantly ($P<0.05$) more efficient than passive exposure in attracting bacteria to MAC agar plates on each sampling date. Moreover, the impaction sampler never yielded significantly higher total bacterial recovery than did device 10 at any of the four post-inoculation intervals. No other combination of air sampling method and duration resulted in more total bacterial colonies on MAC agar on any sampling date than was obtained by applying device 10 of the present invention for about 1 hour. Device 10 produced an overall mean for all four weeks combined of about 66.6 bacterial colonies per MAC agar plate, but all other sampling approaches led to the recovery of about 22.8 or fewer colonies.

All three sampling devices supported the collection of typical *Salmonella* colonies on BG agar plates (Table 2 and FIG. 10). All pre-inoculation air samples were negative for *Salmonella*. At about 1 week after oral inoculation of the hens with *S. enteritidis*, at least 87.5% of the agar plates were positive for *Salmonella* after testing with either the impaction sampler or device 10 for about 20 minutes or after testing by passive exposure for about 3 hours. The frequency of positive results declined in subsequent weeks for all methods, but both the impaction sampler used for approximately 20 minutes and device 10 used for approximately 1 or 3 hours recovered *Salmonella* from at least 37.5% of air samples taken at about 4 weeks post-inoculation. For all four sampling dates combined, no other combination of air sampling method and duration yielded more frequent isolation of *Salmonella* colonies on BG agar than was obtained using device 10 of the present invention: about 62.5% of plates for about 1 hour and about 75% of plates for about 3 hours. During the first two week post-inoculation and for all 4 weeks combined, the electrostatic sampling device when used for about 1 hour or about 3 hours was associated with significantly ($P<0.05$) greater mean numbers of *Salmonella* colonies on BG agar plates than were obtained by passive exposure. No significant differences in the mean numbers of *Salmonella* colonies were evident between the impaction sampler and device 10 of the present invention. However, only device 10 used for about 3 hours collected a mean of at least two typical *Salmonella* colonies per agar plate on each of the four sampling dates.

TABLE 1

Bacterial colonies on MacConkey agar plates exposed to various types of air samples in rooms containing laying hens inocluated with *Salmonella enteritidis*.[A]

| Duration of Sampling | Sample Type[B] | Mean Total Number of Bacterial Colonies | | | | |
|---|---|---|---|---|---|---|
| | | 1 wk PI | 2 wk PI | 3 wk PI | 4 wk PI | All wks |
| 20 minute | Impaction | 21.0[ab] | 23.0[ab] | 39.5[ab] | 7.5[ab] | 22.8[ab] |
| | Electrostatic | 12.8[ab] | 22.5[a] | 29.5[ac] | 9.3[a] | 18.5[ab] |
| | Passive | 3.3[a] | 1.4[b] | 4.4[sd] | 0.1[b] | 2.3[c] |
| 1 Hour | Electrostatic | 68.5[b] | 83.3[a] | 94.0[bd] | 20.5[a] | 66.6[a] |
| | Passive | 13.1[ab] | 6.9[ab] | 55.6[bc] | 2.3[ab] | 19.5[b] |

[A]In each of two trials, 36 orally infected laying hens were housed in individual cages.
[B]Collected using an impaction sampler (2 plates for each sampling duration), device 10 (4 plates each time), or by passive exposure to air (8 plates each time).
[a,b,c,d]Values within columns are significantly different ($P < 0.05$) if they share no common lower-case superscripts.

skilled in the art can make variations without departing from the spirit and scope of the invention.

INDEX OF THE ELEMENTS

1. Batteries
2. Power Switch
3. Voltage Regulator
4. DC Powered High Voltage Power Supply
5. Means for Attaching Batteries
6. Discharge Electrodes
7. Means for Adjusting Electrode Height
8. Collector Means
9. Means for Grounding
10. Portable Electrostatic Sampling Device
11. First Sealed Compartment
12. Second Sealed Compartment
13. Power Light Indicator
14. External Battery Holding Means
17. Base
18. Media
20. Set Screw

What is claimed is:

1. A portable high efficiency electrostatic sampling device comprising:
    (a) at least one discharge electrode,
    (b) a high voltage power supply operatively connected to said at least one electrode,
    (c) a power source operatively connected to said high voltage power supply and at least one discharge electrode, wherein said high voltage power supply effects ionization which generates an electrostatic charge from said at least one electrode which permits capture of viable organisms which remain viable throughout a sampling period and a subsequent incubation period, and
    (d) a grounded, conductive collection surface.

2. The device of claim 1 further comprising a voltage regulator operatively connected to said power source and said high voltage power supply.

3. A method for collecting airborne particulates comprising:
    (a) placing a portable, high efficiency electrostatic sampling device of claim 2 in a vicinity to be sampled,

TABLE 2

Typical *Salmonella* colonies on brilliant green agar plates exposed to various types of air samples in rooms containing laying hens inoculated with *Salmonella enteritidis*[A].

| Duration of Sampling | Sample Type[B] | Mean Number of *Salmonella* colonies (positive plates/total) | | | | | | | | |
|---|---|---|---|---|---|---|---|---|---|---|
| | | 1 wk PI | | 2 wk PI | | 3 wk PI | | 4 wk PI | | All wks |
| 20 minutes | Impaction | 13.0[ab] | (4/4) | 1.0[ab] | (2/4) | 0[a] | (0/4) | 0.8[a] | (2/4) | 3.7[ab] (8/16) |
| | Electrostatic | 6.4[ab] | (7/8) | 0.1[a] | (1/8) | 0.5[a] | (3/8) | 0.3[a] | (1/8) | 1.8[ac] (12/32) |
| | Passive | 0.8[a] | (7/16) | 0.1[a] | (2/16) | 0[a] | (0/16) | 0.1[a] | (1/16) | 0.2[a] (10/64) |
| 1 Hour | Electrostatic | 3.5[bc] | (8/8) | 1.4[ab] | (5/8) | 1.4[a] | (4/8) | 0.6[a] | (3/8) | 1.7[bc] (20/32) |
| | Passive | 0.5[a] | (5/16) | 0.1[a] | (2/16) | 0.3[a] | (3/16) | 0.2[a] | (3/16) | 0.3[a] (13/64) |
| 3 Hours | Electrostatic | 8.6[b] | (8/8) | 2.8[b] | (8/8) | 4.6[a] | (4.8) | 2.3[a] | (4/8) | 4.6[b] (24/32) |
| | Passive | 1.8[ac] | (14/16) | 0.2[a] | (2/16) | 1.6[a] | (7/16) | 0.3[a] | (4.16) | 1.0[ac] (27/64) |

[A]In each of two trials, 36 orally infected laying hens were housed in individual cages.
[B]collected using an impaction sampler, device 10 of the present invention, or by passive exposure to air.
[a,b,c]Values within columns are significantly different ($P < 0.05$) if they share no common lower-case superscripts.

The foregoing detailed description is for the purpose of illustration. Such detail is solely for that purpose and those (b) applying a high negative voltage to at least one discharge electrode to create a strong electrostatic field to airborne particulates wherein said electrostatic field permits capture of viable organisms which remain viable throughout a sampling period and a subsequent incubation period, and (c) collecting at least one viable organism in or on a grounded, conductive material.

4. The method of claim 3 wherein said at least one organism is a microorganism.

5. The device of claim 1 further comprising a first sealed compartment creating a water-tight enclosure of electronic parts.

6. The device of claim 5 further comprising a second sealed compartment creating a water-tight enclosure of said power source.

7. The device of claim 1 wherein said power source is selected from the group consisting of at least one battery, an AC powered adaptor with a DC output, and combinations thereof.

8. The device of claim 1 wherein said grounded, conductive material is selected from the group consisting of water, cell culture media, microbiological media, metal material and conductive carbon.

9. A method for collecting airborne particulates comprising:

(a) placing a portable high efficiency electrostatic sampling device of claim 1 in a vicinity to be sampled, (b) applying a high negative voltage to at least one discharge electrode to create a strong electrostatic field close to a grounded, conductive material wherein said electrostatic field permits capture of viable organisms which remain viable throughout a sampling period and a subsequent incubation period, and (c) collecting airborne particulates in or on said grounded, conductive material.

10. The method of claim 9 wherein said airborne particulates include at least one microorganism.

* * * * *